United States Patent [19]
Eggeling et al.

[11] 4,250,261
[45] Feb. 10, 1981

[54] PROCESS FOR THE MICROBIAL PRODUCTION OF ALCOHOLOXIDASE

[75] Inventors: Lothar Eggeling; Manfred Paschke; Hermann Sahm, all of Jülich, Fed. Rep. of Germany

[73] Assignee: Kernforschungsanlage Jülich Gesellschaft m.b.H., Jülich, Fed. Rep. of Germany

[21] Appl. No.: 55,533

[22] Filed: Jul. 9, 1979

[30] Foreign Application Priority Data

Jul. 10, 1978 [DE] Fed. Rep. of Germany ....... 2830327

[51] Int. Cl.³ .............................................. C12N 9/04
[52] U.S. Cl. ..................................... 435/190; 435/25; 435/28; 435/147; 435/168; 435/930
[58] Field of Search .................. 435/190, 930, 25, 28, 435/4, 147, 168, 247, 255

[56] References Cited

U.S. PATENT DOCUMENTS

4,168,201  9/1979  Wegner ............................. 435/247 X

OTHER PUBLICATIONS

Reuss et al., Chemie-Ingenieur-Technik, vol. 46, No. 16, pp. 669–676, (1974).
Barman, Enzyme Handbook, Supplement I, 1974, pp. 70–71.

*Primary Examiner*—Lionel M. Shapiro
*Attorney, Agent, or Firm*—Karl F. Ross

[57] ABSTRACT

A method of producing alcohol oxidase wherein *Hansenula polymorpha* yeast is cultivated in a nutrient broth containing inorganic nutrient salts of which either the phosphate, nitrate or potassium is present in a cell-growth-limiting concentration at a temperature of 25° to 45° C. and a pH of 4.0 to 6.0 with oxygen being supplied as air for a mixture of air and oxygen. According to the invention, an organic substrate consisting of glycerin, sorbite or xylose, noncatabolite-repressive to alcohol-oxidase is added to the broth in a concentration of 0.1 to 1.0% in a nutrient solution at a rate of 0.03 to $0.15 h^{-1}$.

5 Claims, No Drawings

PROCESS FOR THE MICROBIAL PRODUCTION OF ALCOHOLOXIDASE

FIELD OF THE INVENTION

The present invention relates to the microbial production of alcohol oxidase and, more particularly, to the production of alcohol oxidases by the cultivation of a facultative methanol- consuming yeast, namely Hansenula polymorpha, with the production of a cell mass in the nutrient broth from which the alcohol oxidase is removed.

BACKGROUND OF THE INVENTION

It is known that certain facultative methanol utilizing yeasts, including Hansenula polymorpha, can be cultivated in an inorganic nutrient broth containing inorganic salts, vitamins and a carbon source and/or energy carrier which can be methanol.

In such systems, nutrient solution is continuously added, the cell mass is removed from the culture medium and the alcohol oxidase is recovered therefrom. Practically a steady state system can be provided in which the cell mass is removed at the same rate as the nutrient solution is added or vice versa. The cultivation of the yeast is effected at a pH of 4.0 to 6.0 and a temperature of 25° to 45° C. with the addition or air or/and air/oxygen mixture, the latter being oxygen-enriched air.

Alcohol oxidase is an enzyme which catalyzes the following reaction:

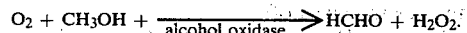

$$O_2 + CH_3OH \xrightarrow{\text{alcohol oxidase}} HCHO + H_2O_2.$$

This enzyme can thus be used for the production of formaldehyde and/or for the production of hydrogen peroxide from methanol. It has also been used analytically for the determination of certain alcohols, generally methanol, ethanol, N-propanol and N-butanol with a measuring system utilizing a so-called enzyme electrode.

It is known in the art that methanol-consuming yeasts such as Candida, Hansenula, Pichia and Torulopsis stains, in cultivation or growth in the presence of methanol, induce a flavin-adenosine-dinucleotide (FAV) containing alcohol oxidase which catalyzes the oxidation of methanol to formaldehyde in a material exchange process.

It has been pointed out in the literature that for the recovery of alcohol oxidase enzyme, the yeast Candida boidinii and Hansenula polymorpha yeast can be used.

In the past, Candida boidinii yeast has been used in batch cultures in a mineral-salt medium with methanol serving as a carbon and energy source with the vitamins biotine and thiamine being added.

These conventional processes are only limitedly effective. It has been pointed out that to achieve a higher cell density (higher density of the produced cell mass) additional methanol can be supplied during the growth or cultivation of the cells in the culture medium (see REUSS, M. et al, Chemie-Ingenieur-Technik, 46, pages 669 ff. (1974).

Upon termination of the yeast cultivation by this technique the yeast cells are found to have a specific activity of alcohol oxidase in the raw extract of 0.3 to 1.0 enzyme units per mg of protein.

In the recovery of alcohol oxidase from the methanol-consuming yeast Hansenula polymorpha, the culture medium is continuously supplied with a nutrient solution containing methanol and the vitamins biotine and thiamine. The quantity of alcohol oxidase obtained in this fashion, with the growth limited by the carbon and energy source methanol and with a growth rate of $0.6\ h^{-1}$ (volume $\times$ volume $^{-1} \times h^{-1}$, i.e. volume rate of growth per total volume per hour), is 7% of the total protein, corresponding to a specific activity in the raw extract of 2.5 to 3.0 enzyme units per mg of protein.

With a growth rate of $0.03\ h^{-1}$ under the same culture conditions, the alcohol oxidase quantity can be about 20% of the total protein so that the specific activity in the raw extract can correspond to 10 to 11 enzyme units per mg protein (see van DIJKEN, J.P.: Arch. Microbiol, 111, pgs. 137 ff, 1976).

After the termination of the cultivation, the enzyme is isolated from the yeast cells by column chromatography and enzyme precipitation.

OBJECTS OF THE INVENTION

It is the principal object of the present invention to provide an improved process for producing alcohol oxidase by microbiological techniques.

Another object of the present invention is to improve upon conventional processes utilizing the yeast Hansenula polymorpha, thereby providing a process for the production of alcohol oxidase having a higher yield in alcohol oxidase per unit of protein produced than the conventional processes.

DESCRIPTION OF THE INVENTION

These objects and others which will become apparent hereinafter are attained, in accordance with the present invention, in a process for the microbiological production of alcohol oxidase utilizing a culture of the facultative methanol consuming yeast Hansenula polymorpha by cultivating the same in an inorganic nutrient broth containing vitamins and methanol as the carbon and energy carrier. Nutrient solution is continuously added to the broth and the cell mass produced by the culture medium is removed and a quantity of the nutrient solution is supplied corresponding thereto. The alcohol oxidase is removed from the recovered cell mass and the reaction is carried out at a pH of 4.0 to 6.0 of the nutrient solution at a temperature of 25° to 45° C. with air or an air-oxygen mixture being supplied.

According to the invention, in addition to the methanol as the carbon and energy source, a substrate is supplied to the system which is not catabolite-repressive of the alcohol oxidase, this substrate being preferably glycerin, sorbite or xylose, although other substrates are conceivable as will be described below.

The additional substrate is added in a concentration of 0.1 to 1.0% in the nutrient broth which is fed at a rate of 0.03 to 0.15 $h^{-1}$.

In the latter case, therefore, nutrient broth is provided at a rate of 0.03 to 0.15 volume of the nutrient solution added per volume of the broth to which the nutrient solution is added per hour. In short, the symbol $h^{-1}$ represents volume per volume per hour.

During the continuous process, which can effectively be a chemical steady state, i.e. a chemostatic equilibrium, the cell mass recovered from the culture medium can correspond to nutrient loss added and from the removed or recovered cell mass the alcohol oxidase enzyme is recovered in the manner previously described, e.g. by column chromatography and enzyme precipitation.

The use of a mixed substrate of methanol and at least one other substance not catabolite-repressive to the alcohol oxidase results in a surprisingly higher enzyme activity, i.e. number of units of enzyme produced per mg of protein.

In short, the cells produced by the cultivation of the present invention show a higher alcohol oxidase activity than cells produced by earlier cultivations.

It has been found to be advantageous, moreover, to provide a nutrient solution containing phosphate, nitrate or potassium in a cell-growth-limiting dosage so that one of these nutrients controls the cell development. This has been found to give still higher yield in alcohol oxidase.

In a preferred mode of carrying out the invention in practice, the mixed substrate is glycerin/methanol or xylose/methanol, serving as the carbon and energy source and is introduced in a nutrient solution in which phosphate is the growth-limiting agent.

The *Hansenula polymorpha* which is preferably used in accordance with the present invention is strain number CBS 4732 as is obtainable from the Centraalbureau voor Schimmelcultures, Julianalaan 67, Delft, Holland. This strain is freely available and accessible to all.

The sulphates added to the nutrient solution, such as glycerin, sorbite or xylose, have been described as non-catabolite-repressive of the alcohol oxidase. Generally any substance capable of acting as a combined substrate with methanol and as a carbon and energy source can be used for this purpose provided it too is noncatabolite-repressive and is an organic compound.

To determine whether any particular substrate is catabolite-repressive or not, it is merely necessary to introduce the substrate together with methanol into the nutrient broth which has been innoculated with the yeast *Hansula polymorpha*. The system is incubated for one to two days and the resulting yeast culture is tested for its enzyme activity. A reduction in the alcohol oxidase over that produced with a control culture utilizing only methanol will demonstrate catabolite-repressive activity whereas an increase in the alcohol oxidase level will show noncatabolite-repressive characteristics. Thus this is a very simple test for determining whether any particular substrate has the desired characteristics.

EXAMPLE I

A nutrient solution is introduced into a 12 liter vessel having a working volume of 7 liters. The nutrient solution had, apart from the yeast innoculant, the following composition:

5 g/l xylose
4 g/l methanol
0.047 g/l $KH_2PO_4$
0.013 g/l $NaH_2PO_4$
0.125 g/l $NaH_2SO_4$
0.4 g/l $K_2SO_4$
0.5 g/l $(NH_4)_2SO_4$
2.5 g/l $NH_4Cl$
0.05 g/l $MgSO_4.7H_2O$
0.7 g/l $NaCl$ 0.5 mg/l $H_3BO_3$
0.04 mg/l $CuSO_4.H_2O$
0.1 mg/l $KI$
0.2 mg/l $FaCl_3.6 H_2O$
0.4 mg/l $MnSO_4.H_2O$
0.4 mg/l $ZnSO_4.7H_2O$
0.2 mg/l $(NH_4)_6Mo_7O_{24}.4H_2O$
0.05 mg/l biotine
1.0 mg/l thiamine
The pH was 5.0.
The temperature of the solution was about 37° C.

The nutrient solution was aerated at a rate of $1v/v_n$ (corresponding to one liter of air per minute of reactor volume) and mechanically agitated with a rotary stirrer at a speed of 1000 RPM per minute. The nutrient solution in the reaction vessel was used to cultivate a yeast *Hansenula polymorpha* of strain number CBS 4732. The culture produced was removed progressively at a rate corresponding to the feed rate of 0.05 $h^{-1}$ of the nutrient solution which has the composition stated above.

Using this process, about 30,000 alcohol oxidase units per liter median were recovered corresponding to 28 units of alcohol oxidase per mg of protein of the cell mass.

EXAMPLE II

The method described in Example I was followed when instead of 5.0 g per liter xylose, 5 g per liter of glycerin was used in the culture medium. This process results in 25,000 alcohol oxidase units per liter of median corresponding to 22 units per mg of protein.

We claim:

1. A method of producing alcohol oxidase which comprises the steps of:
   cultivating *Hansenula polymorpha* yeast in a nutrient broth containing inorganic nutruents, methanol serving as a carbon and energy source, and vitamins in a composition suitable to the production of alcohol oxidase at a temperature of 25° C. to 45° C. and at a pH of 4.0 to 6.0 and with the supply of oxygen to the broth to produce a cell mass;
   adding to the broth during the cultivation thereof an organic substrate noncatabolite-repressive to alcohol oxidase in the form of at least one compound selected from the group which consists of glycerin, sorbite and xylose and in a concentration of 0.1 to 1.0% in a nutrient solution at a rate of 0.03 to 0.15 $h^{-1}$; and
   recovering alcohol oxidase from the cell mass.

2. The process defined in claim 1 wherein said solution contains at least one nutrient selected from the group which consists of phosphate, nitrate and potassium in a cell-growth-limiting concentration.

3. The process defined in claim 1 wherein produced cell mass is removed at least at intervals from said broth and alcohol oxidases is separated from the removed portions.

4. The process defined in claim 3 wherein said solution is added to said broth at a rate sufficient to replace the cell mass removed therefrom.

5. The process defined in claim 1, claim 2, claim 3, or claim 4, wherein the oxygen is introduced into the broth in the form of air or oxygen-enriched air.

* * * * *